United States Patent
Young

(10) Patent No.: US 6,447,794 B2
(45) Date of Patent: Sep. 10, 2002

(54) STOMACH-ACTION MOLLUSCICIDES

(75) Inventor: Colin Leslie Young, 21 Reynolds Road, Wattle Glen Victoria 3096 (AU)

(73) Assignee: Colin Leslie Young, Wattle Glen (AU)

( * ) Notice: Subject to any disclaimer, the term of this patent is extended or adjusted under 35 U.S.C. 154(b) by 0 days.

(21) Appl. No.: 09/899,842

(22) Filed: Jul. 9, 2001

Related U.S. Application Data

(63) Continuation of application No. 09/597,790, filed on Jun. 19, 2000, which is a continuation of application No. 09/029,050, filed as application No. PCT/AU97/00033 on Jan. 22, 1997, now Pat. No. 6,093,416.

(30) Foreign Application Priority Data

Jan. 25, 1996 (AU) ............................................... PN7757
Aug. 19, 1996 (AU) ............................................... PO1708

(51) Int. Cl.$^7$ ............................................. A01N 25/08
(52) U.S. Cl. ....................... 424/408; 424/410; 424/646; 424/647; 424/648; 424/84; 514/502
(58) Field of Search ........................ 424/405, 406–440, 424/84, 646–648; 514/502, 918–920; 426/1, 326, 532, 484

(56) References Cited

U.S. PATENT DOCUMENTS

| | | | |
|---|---|---|---|
| 2,836,537 A | 5/1958 | Skaptason et al. | |
| 5,017,620 A | 5/1991 | Grassman et al. | |
| 5,162,349 A | 11/1992 | Beriger et al. | |
| 5,362,749 A | 11/1994 | Henderson et al. | |
| 5,437,870 A | 8/1995 | Puritch et al. | |
| 6,093,416 A | 7/2000 | Young | |

FOREIGN PATENT DOCUMENTS

| | | |
|---|---|---|
| AU | B-22526 | 8/1988 |
| AU | 81174/91 | 2/1992 |
| AU | B-32232 | 7/1995 |
| WO | 96/05728 | 2/1996 |

OTHER PUBLICATIONS

Australian Patent App. No. 689399 (12203/97) of Colin Leslie Young: vol. 1, Opposition thereto by W. Neudorff GmbH KG, Evidence in Support.
Australian Patent App. No. 689399 (12203/97) of Colin Leslie Young: vol. 2, Opposition thereto by W. Neudorff GmbH KG, Evidence in Support.
Australian Patent App. No. 689399 (12203/97) of Colin Leslie Young: vol. 3, Opposition thereto by W. Neudorff GmbH KG, Evidence in Answer.
Australian Patent App. No. 689399 (12203/97) of Colin Leslie Young: vol. 4, Opposition thereto by W. Neudorff GmbH KG, Evidence in Reply.
Australian Patent App. No. 689399 (12203/97) of Colin Leslie Young: vol. 5, Opposition thereto by Arthur Yates & Co. Limited, Evidence in Support.
Australian Patent App. No. 689399 (12203/97) of Colin Leslie Young: vol. 6, Opposition thereto by Arthur Yates & Co. Limited, Evidence in Support.
Australian Patent App. No. 689399 (12203/97) of Colin Leslie Young: vol. 7, Opposition thereto by Arthur Yates & Co. Limited, Evidence in Answer.
Australian Patent App. No. 689399 (12203/97) of Colin Leslie Young: vol. 8, Opposition thereto by Arthur Yates & Co. Limited, Evidence in Reply.
Australian Patent App. No. 689399 (12203/97) of Colin Leslie Young: vol. 9, Opposition thereto by Arthur Yates & Co. Limited and Opposition thereto by W. Neudorff GmbH KG, Further Evidence.
Kari, F. et al, "Determination of the Reaction Quantum Yield for the Photochemical Degradation fo Fe (III)–EDTA: Implications for the Environmental Fate of EDTA in Surface Waters" *Environ. Sci. Technol.* (1995) v. 25 pages 1008–1017.
Derwent Accession No. 02105X, Class CO1, CH 569405 (CIBA GEIGY AG) Nov. 28, 1975.
Henderson et al, "Problems in developing chemical control of slugs" *Aspects of Applied Biology* (1986) v. 13 pp. 341–347.
Henderson et al., "Control of Slugs with Contact–Action Molluscicides" *Ann. Appl. Biol.* (190) v. 116, pp. 273–278.
Anderegg, "Complexones" in "Comprehensive Co–ordination Chemistry"$1^{st}$ ed. Wilkinson, G. Oxford Pergamon Press 1987, Chapter 20.3 pp. 777–792.
Kelly, Greenwood, Bailey, "Can Different pH Environments in Slug Digestive Tracts Be Exploited to Improve the Efficacy of Mulluscicide Baits" BCPC Symposium Proceedings No. 66: Slug & Snail Pests in Agriculture (1996) 83–90.
Young, "Metal Chelates as Stomach Poison Molluscicides for Introduced Pests, *Helix Aspera, Theba Pisana, Cernuella Virgata* and *Deroceras Reticulatum* in Australia" BCPC Symposium Proceedings No. 66: Slug & Snail Pests in Agriculture(1996) 237–243.
Clark, Coward, Dawson, Henderson, Martin, "Metal chelate Molluscicides: the Redistribution of Iron Diazaalkanolates from the Gut Lumen of the Slug" *Pestic Sci* (1995) 44:381–388.
Henderson, Briggs, Coward, Dawson, Pickett, Bullock, Larkworthy, "A New Group of Molluscicidal Compounds" in BCPC mono 41, Slugs and Snails in World Agriculture, (1989) 289–294.
Henderson, Martin, Parker, "Laboratory and Field Assessment of a new Aluminum Chelate Slug Poison" *Crop Protection* (1990) 9:131–134.

(List continued on next page.)

*Primary Examiner*—Neil S. Levy
(74) *Attorney, Agent, or Firm*—Burns, Doane, Swecker & Mathis, L.L.P.

(57) ABSTRACT

A stomach-action molluscicide including a metal complexone as an active ingredient The term "complexone" as used herein refers to an organic ligand containing at least one iminodiacetic group —N(CH$_2$CO$_2$H$_2$)$_2$ or two aminoacetic groups —NHCH$_2$CO$_2$H which form stable complexes with most cations. Preferably, the complexone is a derivative of ethylenediaminetetraacetic acid.

8 Claims, No Drawings

OTHER PUBLICATIONS

Walker "Studies on the Digestion of the Slug Agriolimax Reticulatum", Ph.D. thesis, Abstract (1969).

Marigomez, Angulo, Saez "Feeding and Growth Responses to Copper, Zinc, Mercury and Lead in Terrestrial Gastropod Arion Ater" *J. Moll. Stud.* (1986) 52:68–78.

Rico, Alvarez, Vallejo, "Preparation of Fertilizers with Rosin and Tricalcium Phosphate Coated Zinc Chelates. Laboratory Characterization" *J. Agric. Food Chem.* (1995) 43:2758–2761.

Material Safety Data Sheet for Multiguard updated Oct. 8, 1996.

NRA Gazette and NRA Internet Data relating to Multicrop Snail and Slug Pellets (Oct. 1996).

Wilkins, Yelin, "The Kinetics of Monomer–Dimer Interconversion of Iron (III)–Ethylenediaminetetraacetate and Related Chelates" *Inorganic Chemistry* (1969) 8:1470–1474.

Schugar, Hubbard, Anson, Gray, "Electrochemical and Spectral Studies of Dimeric Iron (III) Complexes" *J. Am Chem Soc* (1969) 91:71–77.

Gustafson, Martell, "Hydrolytic Tendencies of Ferric Chelates" *J. Phys Chem* (1963) 67:576.

Scharzenbach, Heller, "Komplexone XVIII. Die Eisen(II)– und Eisen(III)–komplexe der Athylendiamin–tetraessigsaure und ihr Redoxgleichgewicht" *Helv Chem Acta* (1951) 34:576–591.

Motekaitis, Martell, "New Multidentate Ligands. XXV. The Coordination Chemistry of Divalent Metal Ions with Diglycolic Acid, Carboxymethyltartronic Acid and Ditartnic Acid" *J. Coord. Chem.* (1984) 13:265.

STOMACH-ACTION MOLLUSCICIDES

This application is a continuation of application Ser. No. 09/597,790, filed on Jun. 19, 2000, which is a continuation of application Ser. No. 09/029,050 filed Feb. 18, 1998 now U.S. Pat. No. 6,093,416 which was a national stage filing under 35 U.S.C. § 371 of International Application No. PCT/AU97/00033 filed on Jan. 22, 1997, which International Application was published by the International Bureau in English on Jul. 31, 1997.

FIELD OF THE INVENTION

The present invention relates to stomach-action molluscicides, stomach poisons or edible baits containing them and their use in killing, controlling and/or inactivating molluses, in particular, slugs and snails.

BACKGROUND TO THE INVENTION

Slugs and snails are major pests of agriculture in many parts of the world. Their biology tends to favour activity in moist conditions such as habitats which are continually wet and temperate regions, especially during rainy summers and autumns. As a consequence, their potential for damage is considerable.

The ecologies of different types of molluscs, which can be either terrestrial or aquatic, are very different and they usually require different types of treatment. The snail species *Theba pisana, Cemuella virgata, Helix aspersa* and *Achatina* spp and the slug species, *Arion hortensis, Milax budapestensis, Deroceras reticulatum* and *Limax maximus* are of particular interest as targets. The common garden snail, *Helix aspersa*, and the grey field slug, *Deroceras reticulatum*, are common garden pests throughout temperate Australia. These pests have established themselves in many parts of the world, adapting to a wide range of climatic conditions. They rarely increase in numbers above 20 per square meter but cause damage by feeding, with minor damage due to the mucus on which they move. *Helix aspersa* is, in general, a nocturnal feeder and in the daytime remains hidden on the underside of leaves, under rocks or in cracks in the soil. It flourishes in moist conditions. On the other hand, there are a group of snails which have been introduced into Australia in the twentieth century. The areas in which these are pests (often over 200 per square meter) are still expanding. These are the white Italian snail, *Theba pisana* and the vineyard or Mediterranean snail, *Cernuella virgata*, which can survive long hot summer temperatures by aestivating on weeds and fence posts, retreating into their shells and secreting a hard mucous film to reduce moisture loss and rest. These snails are of some concern to Australian farmers because they also aestivate on the heads of cereal stalks in November and December and during harvest, they clog up the machinery and contaminate the grain, making it either unacceptable or forcing it to be downgraded. There are very significant variations of the pest numbers and in a bad year it is uneconomic to harvest substantial areas of crops. In cold climates, *Theba pisana* hibernates in winter. The slug, *Deroceras reticulatum*, is found throughout temperate areas of the world and it is the major slug variety found in both Australia and the United Kingdom.

Significant crop damage by molluscs also occurs in northern Europe, the Middle East, North and Central America, South East Asia, Japan and New Zealand. In many cases, the rise to pest status of the slug or snail in question is a consequence of change—either in distribution (as in the case of accidental or deliberate introductions) or in agricultural practice, where new crops or systems of cultivation may enable populations to rise to pest levels. For example, approximately two-thirds of the molluscicides in the United Kingdom are used on winter wheat and winter barley. After harvesting, there is a significant amount of stubble left behind. It is present agricultural practice to drill seeds of the next crop directly into the soil, without removing the stubble of the previous crop by, for example, burning. Slugs, which have buried themselves in the soil, move along into these drill holes and eat the inside out of the new seed, thereby potentially destroying the whole planting. Slugs are therefore a major agricultural pest.

Devising methods of controlling these pests presents a formidable task. Control methods involve cultivation practices, chemical and biological methods. Cultivation procedures that remove or make the habitat of the mollusc less attractive, are usually less expensive. Biological control by introduction of natural predators is a preferred method because, in principle, the predator could be snail specific and not harm native snails or non-target organisms. However, very extensive testing is required and, once predators have been introduced, it is very difficult to reverse the process and to remove them. Chemical methods (molluscicides) involve the use of a contact or stomach poison, an irritant or a feeding depressant.

The environment which the mollusc inhabits is generally treated with the molluscicide which is then ingested by the mollusc. Since most snails and slugs thrive in moist conditions, any effective molluscicide should be effective under these conditions. This feature of appropriate water resistance has major implications in broad-acre agriculture, where one treatment is preferred rather than multiple applications throughout the crop season. In this case, it is desirable to have a balance between water resistance and efficacy to prevent the pellets functioning as poisons after the crop has been harvested and livestock has moved into the area to feed. In addition, in areas of very high moisture content there should be effective water-proofing to ensure the poison is maintained in an ingestable form for a sufficient time to permit adequate exposure to the molluscs. Since moisture is essential for slug and snail activity, damage is likely to be more severe on heavy soils due to their greater moisture retention. However, damage is not restricted to heavy soils. Slug and snail activity is encouraged by high levels of organic matter which often provides a moist environment. Green manure crops and old crop residues used in the compost heap often allow populations to build up quickly. Dense leafy plants, such as brassica and curcubitis, provide a moist humid canopy under which snails and slugs thrive. Temperature also affects the level of slug and snail activity. Indeed, this activity peaks around 15–20° C. and decreases markedly below 5° C. and above 30° C. Furthermore, low temperatures significantly delay the hatching of slug eggs. Most slug and snail species are nocturnal feeders. Hence, watering of gardens in the evening often provides an environment which encourages increased feeding activity.

Molluscicides for use against slugs and snails can be divided into three groups. These are contact-action molluscicides, such as aluminium and copper sulfate crystals, which are applied to the area inhabited by the snail or slug and are taken up passively when the snail or slug moves in this area; irritant powder molluscicides, such as silica grains, which act by being taken up in the snail's or slug's locomotion mucus; and stomach-action molluscicides such as metaldehyde and methiocarb pellets, which are ingested by the mollusc.

Contact-action molluscicides are generally applied in the form of sprays and dusts to crops and the mollusc receives a fatal dose of toxin by moving over the crop. Molluscs present problems of delivery of the toxin because their relatively large size means that a large dose of toxin is necessary. They are also relatively inmobile and may remain concealed in comparative safety for long periods. These problems are further complicated by the layer of mucus which invests molluscs. Irritant materials stimulate mucous production and can be sloughed off and left behind in a discarded mucous coat. As the mucus is largely composed of water, the water-solubility of candidate contact poisons is therefore a prerequisite if they are to be able to penetrate the mucous barrier. However, hydrophilic properties in a toxin also increase the rate at which it is diluted by rain and leached into the soil.

Delivery of effective amounts of bait is also a problem. A sufficient amount of poison must be ingested to ensure a lethal dose. In general, most toxic compounds are also repellent and the interaction of toxicity with repellency prevents the ingestion of sufficient poison to kill the mollusc. There are three major effects of molluscs ingesting poison baits. Firstly, there is a possible repellency away from the crop by the bait. Secondly, ingestion of the bait may cause reduced feeding and thirdly, the poison may kill the snail or slug involved.

Until the mid 1960's, the most effective molluscicide was metaldehyde which is a tetramer of acetaldehyde. In Europe, it was known only as a solid fuel, until its molluscicidal properties were discovered accidentally in France by farmers who found dead and dying snails on and around metaldehyde tablets discarded after use in camping stoves. Metaldehyde is toxic at high concentrations and an irritant at lower concentrations, causing mucous secretion and eventual desiccation. A disadvantage is its dependence on high temperature and low humidity for its maximum effect and there is a high recovery rate amongst molluscs which are able to reverse the water deficit caused by the excess mucous secretion that metaldehyde stimulates. Under optimal conditions, slugs immobilised and desiccated by metaldehyde will not survive if trapped in the open and exposed to sunlight. Unfortunately, it is under damp conditions and at lower temperatures when metaldehyde is least effective that terrestrial slugs and snails are most active and yet, at higher temperatures, snails are aestivating and not feeding. There is only a very limited period of time during which snails are feeding and the temperature is high enough for metaldehyde to be effective.

In the mid 1960's, it was found that carbamate compounds such as methyl carbamate were as toxic to molluscs as metaldehyde. Carbamate compounds cause inhibition of cholinesterases which are the enzymes involved in synaptic nervous transmission in a wide range of animals and their mode of action on insect pests has been extensively studied, particularly in connection with the development of resistance. The methyl carbamate most widely used as a molluscicide is methiocarb (3,5-dimethyl-1,4-methylthiophenyl-N-methylcarbamate). The effectiveness of methiocarb is compromised less by low temperatures and high humidity than metaldehyde which is a major advantage, since pest damage often occurs in conditions where metaldehyde is least well suited. However, methiocarb (an active insecticide and acaricide) is more toxic to non-target organisms such as beneficial insects and earthworms than metaldehyde. Although farmers presently tend to use methiocarb, they would prefer not to because of these highly poisonous characteristics and the fact that sheep often graze in areas that require treatment for snails and slugs. For example, in South Australia there are flood-irrigated pastures for sheep and recently, a high incidence of the conical variety of snail, *Cochlicella barbara*, has been detected. Therefore, any effective molluscicide used under these conditions would have to be effectively water-proofed in addition to not being toxic to the sheep. Methiocarb is effective on *Theba pisana* but in view of its insecticidal activity and toxicity to earthworms, its use for this snail variety also has severe drawbacks.

There is considerable evidence to indicate that metal salts used as contact poisons are toxic to molluscs (Glen, D. M. and Orsman, I. A., in "Comparison of molluscicides based on metaldehyde, methiocarb and aluminium sulphate," Crop Protection, (1986), 5, 371–375.) In particular, iron and aluminium salts have been investigated in this regard in some detail in the United Kingdom (Henderson et al, "Aluminium(III) and Iron(III) complexes exhibiting molluscicidal activity," Australian Patent AU-B-22526/88). These workers concluded that the effectiveness of the molluscicide was dependent on a number of variables but the chelating of the trivalent iron gave very significantly better results than the unchelated salts. In addition, these workers found that the inclusion of the poison in a bait, as a pellet, gave significantly better results than the direct application of molluscicide to the soil or application of the bait as a powder to the soil. Details of the bait formulation were given without discussion of differences that might be expected from other formulations. Such differences are most probably significant in determining the amount of chelate required for effective control. In field conditions, the efficacy and activity of many metal salts is greatly attenuated by both dilution and the metal ions becoming chemically bound in the soil and being unavailable for toxic action. Proposed contact-action metal poisons such as aluminium tris(acetylacetonate) ("Al (acac)")$_3$ are expensive to manufacture and are therefore not economically feasible for use in the home garden or for horticulture or broad-acre application. Various metal salts are marketed as contact molluscicides and are indeed toxic, but it is debatable whether they are effective under field conditions. As contact-action poisons, they are insufficiently persistent and too repellent to be used in baits. For these reasons, molluscicides used against terrestrial (as opposed to aquatic) targets are usually delivered in the form of stomach-action poisons in baits.

One of the other major problems with stomach-action poisons in that they are often consumed by non-target organisms such as domestic animals, birds and children. In normal agricultural and veterinary applications, the preparations are usually very dilute when applied. However, when baits are used this is not the case and there is always a possibility that the bait will be consumed by a non-target organism Accidental poisoning of non-target organisms is particularly common in the case of snail and slug bait pellets. It is hard to arrive at a reliable figure for poisoning of dogs, cats and native animals, but in Australia about 10,000 poisonings per annum with perhaps as high as 40–50% being fatal is probably a reasonable estimate. A requirement accordingly exists for molluscicides which are effective against snails and slugs, but which substantially minimize the health and environmental risks and cost limitations of the molluscicides currently available on the market.

There are a number of published efficacy trials which indicate that Ferric sodium EDTA (Iron(III) EDTA or ferric EDTA) salt is an effective contact-action molluscicide. Research has been conducted on a number of iron and aluminium compounds as contact poisons against the slug *Deroceras reticulatum* (Henderson, I. F. and Martin, A. P., in "Control of slugs with contact-action molluscicides," An. Appl. Biol., (1990), 116, 273–278). These workers reported two types of experiments, one in which the slugs were confined to a treated glass surface and one using wet soil in a laboratory test. Unchelated salts were effective poisons when applied to a glass surface, but were rapidly deactivated when applied on wet soil. Chelation of both metals with organic ligands retarded the rate of attenuation on wet soil. These workers also reported a field trial in which chelated iron in a broadcast application applied at 40 kg active ingredient per hectare, or in a bait formulation applied at 1.32 kg/ha of active ingredient was effective against *Deroceras reticulatum* and *Arion* spp. They concluded that "on the available evidence, the bait formulation was apparently more efficient, an application rate of 1.32 kg active ingredient leaving 586 slugs dead on the surface within three days while with the broadcast formulation applied at 40 kg active ingredient per hectare, only 204 were recorded dead on the surface in the same period." Iron(III) 2,4-pentanedionate appears to be more toxic than Iron(III) EDTA and although it is difficult to quantify the difference, it appears that on wet soil after 10 days, the 2,4-pentanedione is about twice to three times as toxic. Details of the bait formulation were not given but these are most probably significant in determining the amount of chelate required for effective control.

SUMMARY OF THE INVENTION

The inclusion of metal chelates as the active ingredient in stomach-action poisons in accordance with the invention, however, offers considerable advantages over the presently used stomach-action molluscicides, metaldehyde and methiocarb. The present invention concerns the inclusion of a complexone as the chelating ligand to function as the active ingredient in stomach-action poisons. Selected complexones are considerably less toxic to mammals than methiocarb or metaldehyde. Indeed, they are used in medical applications to relieve anaemia. Such complexones are often used in trace-element mixes in situations where a plant is suffering from an iron deficiency. The effectiveness of such complexones is not very temperature- or humidity-dependent, being comparable with methiocarb in this respect. They are neither insecticides nor acaracides and snail and slug pellets based on such compounds will not kill earthworms or the (mainly beneficial) carabid beetles. The term "metal complexone" is used herein in its broadest sense and refers to a chelate of a metal with at least one ligand of the complexone type.

The term "complexone" as used herein refers to an organic ligand containing at least one iminodiacetic group —N(CH$_2$CO$_2$H)$_2$ or two aminoacetic groups —NHCH$_2$CO$_2$H which form stable complexes with most cations. Suitable complexones include those disclosed in Wilkinson, G., "Comprehensive Coordination Chemistry", Volume 2, Chapter 20.3, pp 777–792 which is incorporated herein by reference.

Preferably, the complexone is a derivative of ethylenediaminetetraacetic acid (hereinafter referred to as "EDTA") as shown in formula (I) below:

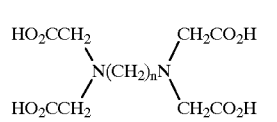

(I)

wherein n is an integer, preferably from 1 to 6.

Other examples of suitable complexones include those having more than four acetic acid residues as shown in formula (II) below:

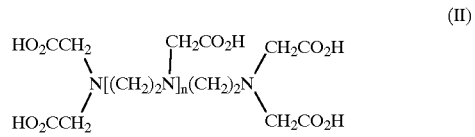

(II)

wherein n is an integer, preferably from 1 to 3 or as shown in formula (III) below:

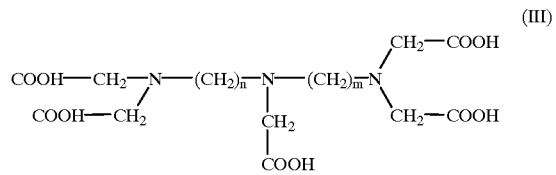

(III)

wherein n and m are integers, preferably from 1 to 4.

While the major complexone utilized in the present invention is EDTA, other complexones, in particular, those having substituents such as hydroxy groups which coordinate to the metal ion more strongly, such as EDDHA, or those which display increased stability due to the presence of an additional coordinating group, such as DPTA, have also been utilized in the trials. Other chelates investigated include ferric sodium ethylenediaminebis[(2-hydroxyphenyl)acetic acid] ("FeEDDTA") and ferric sodium diethylenetriaminepentaacetic acid.

According to one aspect of the present invention, there is provided a stomach-action molluscicide which includes a metal complexone as an active ingredient.

Preferably, the metal complexone includes hydroxy- and non-hydroxy-metal complexones. Most preferably, the active ingredient is an hydroxy-metal complexone.

Typically, the stomach-action molluscicide has a pH above 7. Preferably, the pH is between about 7 and 10. Most preferably, the pH of the molluscicide is about 8.

Typically, the metal of the metal complexone is selected from the group of Group 2 metals, transition metals or Group 13 metals. Preferably, the metal is selected from the group of magnesium, aluminium, manganese, iron, copper or zinc.

Preferred metal complexones include iron(II) and iron (III), copper and zinc EDTA. Iron EDTA and copper EDTA are preferred with iron EDTA being the most preferred. Iron EDTA is also not harmful to the environment as it is widely used as a source of iron for plants and to a limited extent animals in horticulture and agriculture.

Typically, the complexone comprises at least one iminodiacetic group or two aminoacetic groups, the complexone forming a stable complex with the metal. Preferably, the complexone has at least four acetic acid groups. More preferably, the complexone is ethylenediaminetetraacetic acid (EDTA). Most preferably, the active ingredient in the molluscicide is the hydroxy-metal complexone, [Fe(OH)EDTA]Ca which can dimerise to give [EDTAFe—O—FeEDTA].2Ca. Anions [Fe(OH)EDTA]$^{2-}$ and [EDTAFe—O—FeEDTA]$^{4-}$ are important species and it appears that the inclusion of Ca$^{2-}$ is advantageous as it eventually replaces the chelated iron.

In a preferred form of the present invention, the molluscicide is advantageously presented in the form of a stomach poison together with a carrier. The carrier usually includes a mollusc food such as a cereal, for example, wheat flour, bran, arrowroot or rice flour, carrot; beer; rice hulls; comminuted cuttle fish; starch or gelatin so that the mollusc is attracted to the edible bait. Non-nutrient carriers of interest include non-nutrient polymeric materials, pumice, carbon and materials useful as carriers for insecticides. The poison or bait may also contain other additives known in the art such as mollusc phagostimulants for example sucrose or molasses; lubricants such as calcium or magnesium stearate, talc or silica; binders which are suitably waterproof, such as paraffin wax, white oil or casein; and flavouring agents such as BITREX® which imparts a bitter taste and renders the poison or bait less attractive to non-target organisms. In order to inhibit deterioration of the poison or bait, preservatives such as sodium benzoate, vitamin E, alpha-tocopherol, ascorbic acid, methyl paraben, propyl paraben or sodium bisulphite may also be included. Preferably further, the waterproofing agent comprises a fatty acid alcohol in an amount between 1% to 5% by weight of the total composition of the poison. More preferably, the fatty acid alcohol is selected from the group of $C_{16}$–$C_{18}$ fatty acid alcohols. Most preferably, the $C_{16}$–$C_{18}$ fatty acid alcohols comprises about 5% by weight of the total composition of the poison and the $C_{16}$–$C_{18}$ fatty acid alcohol is HYDRENOL MY manufactured by Henkel Corporation. The waterproofing of the bait is also believed to be improved if the density of the bait is increased since the less porous the composition, the more effectively waterproofed it becomes.

To improve the density of the acual mixture before pelletising to reduce the airborne content and thus wastage of the mixture, a filler is added to the carrier. Preferably, the filler is either $CaCO_3$ or $K_2CO_3$. Typically, the poison or bait contains about above 1% and not exceeding 5% of a metal carbonate as a filler. When the metal carbonate is $CaCO_3$, the preferred concentration is about 2–3% by weight. When the metal carbonate is $K_2CO_3$, the preferred concentration is about 4–5% by weight. A combination of $CaCO_3$ and $K_2CO_3$ may also be used.

Serendipitously, such a metal carbonate additionally serves to adjust the pH of the poison or bait and it was found that the efficacy increased with an increase in pH. It was found through trials carried out using various amounts of $CaCO_3$ and $K_2CO_3$ combined, that a balance needs to be struck between the pH and the attractiveness of the bait to the molluscs. If the bait is too acidic, it has been found that the efficacy is reduced. Conversely, if the bait is too alkaline this also deters feeding. Typically, the poison or bait has a pH about above 7 and not exceeding 10. Preferably, the pH of the poison or bait is about 8. Preferably, the agent used to adjust the pH is $K_2CO_3$ together with $CaCO_3$. A stomach poison having a neutral or alkaline pH has proved to be more efficacious than one having an acidic pH. The $K_2CO_3$, together with the $CaCO_3$, used as a filler and which adjusts the pH to about above 8, aids in the formation of the active ingredient, [Fe(OH)EDTA]Ca. The person skilled in the art will appreciate that the behaviour of ferric EDTA in solution and at equilibrium is strongly determined by its speciation. At a pH of between 7 and 10, the species present in the majority is $[Fe(OH)EDTA]^{2-}$ with [Fe(III)EDTA] being present in the minority. According to F. G. Kari et al, Environ. Sci. Technol., (1995), 29, 1008, at a pH of about 8 to 8.5, there is virtually no [Fe(III) EDTA] species present at all.

Preferably, the active ingredient comprises at least 6% by weight of the total composition of the molluscicide. More preferably, the active ingredient comprises about 6% to about 12% by weight of the total composition of the molluscicide when the active ingredient is [Fe(OH)EDTA]Ca or its dimer[EDTAFe—O—FeEDTA].2Ca. Most preferably, [Fe(OH)EDTA]Ca comprises about 9% by weight of the total composition.

According to yet another aspect of the invention, the active ingredient comprises a metal complexone in combination with at least one other molluscicide. Typically, the other molluscicide is selected from metaldehyde or methiocarb, wherein the other molluscicide is in a synergistic relationship with the metal complexone.

The molluscicide is advantageously presented in a solid form such as tablets, powders, granules or pellets. Those skilled in the art will appreciate that it is preferable to prepare the products the subject of the invention in a form that is easy for consumers to use. Pellets, for example, can be easily scattered from a box across the area to be protected. Preferably, the molluscicide is in the form of a pellet. More preferably, the pellet is between 2.5 and 4 mm long. Most preferably, the pellet is 3 mm long.

According to another aspect of the invention, the method of preparation of the stomach-action molluscicide in pellet form includes the steps of:
(i) blending the molluscicide and elements of the carrier together to form a blended composition;
(ii) heating the blended composition for about 1 to 5 minutes in the presence of steam at an ambient temperature of between about 80 and 100° C.;
(iii) maintaining the bended composition at the ambient temperature for between 10 and 30 seconds; and
(iv) forming the blended composition into one or more pellets.

Preferably, step (ii) is carried out at about 90° C. for about 2 minutes, whereafter step (iii) is carried out for about 15 seconds. Preferably, the blended composition is formed into pellets by extrusion.

The term "stomach-action molluscicide" is used herein in its broadest sense and includes a molluscicide which is capable of being ingested into the stomach of the mollusc in an effective amount so as to kill and/or inactivate the mollusc.

EXAMPLES

The invention will now be illustrated with reference to the following non-limiting Examples.
Study of the effectiveness of Fe EDTA pellets and powder compared with metaldehyde and methiocarb pellets The first set of examples are where the product which is the subject of the present invention, was tested and compared with other products currently registered and in the Australian market place and other representative products available elsewhere in the world. The most commonly used home garden pellets in Australia based on metaldehyde are sold under the brand name of DEFENDER™. It may be argued that DEFENDER™ pellets which contain 1.5% metaldehyde are not the best metaldehyde pellets available. However, additional trials using pellets containing 6% metaldehyde have also been carried out and very similar results were obtained. Additional trials have also been carried out comparing the product of the present invention with methiocarb-based pellets. Methiocarb-based pellets account for about 20% of pellets used in Australia and are widely used elsewhere in the world.

The baits, which are the subject of the present invention, are based on bran/wheat flour and are typical of common baits used throughout the world. The known attractiveness of bran/wheat flour baits in the industry made it unnecessary for further experimentation in this area.

To test the efficacy of the baits, which are the subject of the present invention, experiments were set up keeping the following variables in mind:
(i) bait formulation;
(ii) soil type;
(iii) concentration of the active ingredient;
(iv) species of mollusc; and
(v) temperature (range of maximum daily temperature).

Two different bait formulations were used, the first, low bran type, consisted of bran and wheat flour in the ratio of 1 part bran to 4 parts flour, together with small amounts of calcium stearate as a die lubricant, a binder, a filler and a mould inhibitor. The second, high bran type consisted of wheat flour and bran in approximately equal proportions by weight together with a small amount of oat meal (lubricant), a small proportion of sugar (1–2%), a filler and a mould inhibitor. The control treatment involved providing the snails and slugs with carrot for food unless otherwise specified.

The composition of the Fe EDTA pellets and powder was as follows:

655 g/kg wheat flour (for low bran) or 380 g/kg wheat flour (for high bran);

160 g/kg bran ("low bran") or 315 g/kg bran("high bran");

20 g/kg oat meal (high bran)

20 g/kg calcium stearate;

90 g/kg ferric sodium EDTA;

20 g/kg $CaCO_3$;

5 g/kg $K_2CO_3$ 20 g/kg sodium benzoate;

0.2 g/kg BITREX® (denatonium benzoate); and 40 g/kg white oil.

It was established in a number of preliminary trials that ferric EDTA was toxic to *Helix apersa* and *Deroceras reticulatum* as a contact poison on a smooth glass surface. Subsequent trials compared the effective toxicity of methiocarb, metaldehyde bait pellets and ferric EDTA pellets and ferric EDTA bait powder to *Helix aspersa* and the effective toxicity of ferric EDTA to *Deroceras reticulatum*. Limited trials were carried out on *Theba pisana* (the white Italian snail), *Cernuella virgata* (the vineyard snail), *Limax maximus* and Cochlicella spp. These trials confirmed that the particular bait formulation together with 8.5–9% ferric EDTA was effective in control of molluscs.

There are many possible variables to consider when evaluating snail or slug pellets. Field trials are often poorly controlled and it is often difficult to arrive at unambiguous conclusions. It is possible to apply extensive statistical analysis to poorly designed or controlled experiments. However, a series of simple experiments in which the variables are controlled lead to unambiguous conclusions with no need for detailed statistical analysis. It was decided to compare the pellets under laboratory conditions which could closely mimic controlled field conditions but would not present problems arising from incomplete collection and counting of dead specimen or non-uniform distribution of snails in the trial patches. No attempt was made to control the diurnal temperature or the length of daylight, even though it was known that these factors do play some part in snail and slug feeding activity but their role is minor compared with the effect of temperature.

It should be noted that trials on slugs are particularly difficult on account of three factors. Firstly, it is difficult to distinguish between moribund and dead slugs. Secondly, slugs bury themselves in soil and it is often difficult to find dead slugs which have decomposed. Thirdly, it is believed that bacteria from dead slugs often infect and subsequently kill other slugs.

In this study, two types of "plot" were employed. The first type of plot consisted of about 1 cm depth of sandy loam or potting mix placed in a seed tray of approximate dimensions 30×25 cm. The top was covered with a 3 mm glass sheet of which about 70% was covered with black, polythene film. The polythene film was attached with adhesive tape (on the outside), so that the snails or slugs were able to rest on a smooth surface out of direct sunlight. For the second type of plot, a polycarbonate "food storage container" of 175 mm diameter and 80 mm height was employed, four air holes of 2 mm diameter were made in the lid of each container. These containers were used as it was thought that, in the case of *Theba pisana*, *Cernuella virgata* and *Cochlicella barbara* eggs might be laid in the soil and if the seed trays were used extensive precautions were necessary to avoid introducing these snails to areas where they were not previously established. The smaller containers were used to study *Deroceras reticulatum* and the soil replaced by a layer of absorbent paper or a thin layer of soil. This procedure was used because slugs often buried themselves in the soil and were difficult to find without disturbing the soil. It was often difficult to establish if buried slugs were alive or dead.

Unless otherwise specified, the common garden snail, *Helix aspersa* was used in the Examples. The control treatment involved providing the snails and slugs with food, carrot and cabbage leaves in Example 1 and carrot in the remaining Examples. The effectiveness of slug pellets on moist potting mix was studied during spring under natural climatic conditions. In this period, snails were active in the garden as a result of a cool damp spell. While the ideal feeding temperature for snails and slugs is around 20° C., the temperature should be about above 10° C. because at temperatures below this, feeding is considerably reduced.

In Examples 1 to 4, Fe EDTA pellets and powder were compared with metaldehyde pellets marketed under the trade name DEFENDER™. DEFENDER™ pellets contain 1.5% metaldehyde. The pellets were compared under laboratory conditions which would closely mimic controlled field conditions, but would not present problems arising from incomplete collection and counting of dead specimens or non-uniform distribution of snails in the trial patches.

Example 1

This Example involved 3 replicate "plots" of 4 different treatments. Each "plot" consisted of a 250×300 plastic tray containing moist potting mix which was covered by a sheet of glass. Black polythene which covered about 65% the top of the tray was placed over the glass sheet so that it provided a refuge for the snails. About 50 grams of fresh carrot slices and 100 grams of fresh cabbage leaves were placed on top of the moist potting mix in opposite corners of each of the twelve seed trays. Six snails were placed in one of the other corners of each of the twelve seed trays at dusk. Metaldehyde pellets were spread more or less uniformly across three of the trays and the Fe EDTA pellets were similarly spread across three other trays. In the other three trays, Fe EDTA powder was spread about 3–5 cm away from the sliced carrot and cabbage leaves. The snails were observed after 3 days and 6 days with any dead snails being removed and their numbers noted. It was difficult to establish whether some of the snails were dead or merely poisoned and inactive. Only those snails which appeared to be decomposing were counted. The results are given in Table 1 below. It was noticed that the amount of food remaining in the three (×3) treatment plots was greater than in the control. This was not assessed quantitatively. Since after three days the number of active snails in the control plots were on average more than double that in the treatment plots, it would be misleading to assert that the feeding of active snails was reduced. Obviously dead snails did not consume food and live, but poisoned inactive snails did not consume much if any food.

TABLE 1

Comparison of efficacy of Fe EDTA pellets and powder with metaldehyde.

| Control | 1/6 | 0/6 | 0/6 | 1/18 |
|---|---|---|---|---|
| Metaldehyde | 2/6 | 3/6 | 5/6 | 10/18 |
| Fe EDTA pellets | 3/6 | 3/6 | 6/6 | 12/18 |
| Fe EDTA powder | 2/6 | 2/6 | 3/6 | 7/18 |

Example 2

This Example was the same as Example 1 except that no powder treatment was involved and each treatment was replicated four times. Furthermore, the food used was only about 100 g of freshly sliced carrot with no cabbage leaves being included. The number of snails after 6 and 8 days were recorded and are given in Table 2 below. The average daily temperature of this trial was about 5° C. cooler than in Example 1. The results show that the effectiveness of metaldehyde as a poison is very temperature sensitive whereas for ferric EDTA, the main effect is due to a decrease in general activity such as feeding which causes the kill to be somewhat slower than in Example 1. Ferric EDTA is clearly very much more effective at lower temperatures than metaldehyde pellets.

TABLE 2

Comparison of the efficacy of Fe EDTA pellets with metaldehyde at low temperature

| Control | 0/6 | 0/6 | 0/6 | 0/6 | 0/24 |
|---|---|---|---|---|---|
| Metaldehyde | 1/6 | 0/6 | 2/6 | 0/6 | 3/24 |
| Fe EDTA pellets | 4/6 | 5/6 | 5/6 | 6/6 | 20/24 |

Example 3

This Example was conducted using Zeneca (metaldehyde), BIO® PBI (metaldehyde) and 9% Fe EDTA within a temperature range of 18–29° C. using carrot as the feed and high bran in the bait formulation. The dead snails were removed and counted after 7 days. The results are shown in Table 3.

TABLE 3

Comparison of the efficacies of different brands of metaldehyde with 9% Fe EDTA.

| Control | 0/3 | 0/3 | 0/3 | 0/3 | 0/3 | 0/3 | 0/3 | 0/3 | 0/24 |
|---|---|---|---|---|---|---|---|---|---|
| Zeneca (Metaldehyde) | 2/3 | 3/3 | 2/3 | 3/3 | 1/3 | 2/3 | 2/3 | 1/3 | 16/24 |
| BIO ® PBI (Metaldehyde) | 0/3 | 1/3 | 1/3 | 1/3 | 0/3 | 2/3 | 0/3 | 2/3 | 7/24 |
| 9% Fe EDTA | 3/3 | 3/3 | 3/3 | 2/3 | 3/3 | 3/3 | 3/3 | 3/3 | 23/24 |

Example 4

This Example was the same as Example 2, except that the treatments were control, metaldehyde, methiocarb marketed by Yates and 9% Fe EDTA. The results are given in Table 4 below. The weather conditions were warm and dry and there was considerably less snail activity than in Example 2. The lower kill rate was expected as the amount of feeding was reduced.

TABLE 4

Comparison of the efficacies of meltaldehyde, methiocarb and 9% Fe EDTA.

| Control | 0/6 | 0/6 | 0/6 | 0/18 |
|---|---|---|---|---|
| Metaldehyde | 4/6 | 4/6 | 4/6 | 12/18 |
| Methiocarb | 3/6 | 2/6 | 3/6 | 8/18 |
| Fe EDTA pellets | 2/6 | 3/6 | 4/6 | 9/18 |

Summary

Examples 1 to 4 show that the Fe EDTA pellets worked well, the metaldehyde pellets worked moderately well, but the methiocarb and the Fe EDTA powder was less effective. However when using very moist potting mix fairly poor results for the powder would be expected as it would dissolve in the moisture and be taken up by the soil.

In Example 5, the efficacy of various concentrations of Fe EDTA were trialed.

Example 5

This Example was the same as Example 4, except that the treatments were control and pellets containing 1%, 2.5%, 6%, 9%, 12%, 16% and 20% Fe EDTA. The results are given in Table 5 below. The weather conditions were warm and dry and there was considerably less snail activity than in Example 2. Dead snails were removed and counted after 6 days. The lower kill rate (compared to Example 2) was expected as feeding was reduced.

TABLE 5

Comparison of the efficacies of varying concentrations of Fe EDTA used in the pellets.

| Control | 0/6 | 0/6 | 0/6 | 0/18 |
|---|---|---|---|---|
| Fe EDTA 1% | 2/6 | 0/6 | 1/6 | 3/18 |
| Fe EDTA 2.5% | 0/6 | 0/6 | 1/6 | 1/18 |
| Fe EDTA 6% | 2/6 | 2/6 | 4/6 | 8/18 |
| Fe EDTA 9% | 2/6 | 3/6 | 4/6 | 9/18 |
| Fe EDTA 12% | 3/6 | 3/6 | 5/6 | 11/18 |
| Fe EDTA 16% | 3/6 | 4/6 | 3/6 | 10/18 |
| Fe EDTA 20% | 6/6 | 3/6 | 4/6 | 13/18 |

Summary

The results of Example 5 indicate that the proposed 9% Fe EDTA is appropriate. Slightly higher concentrations may give slightly higher kill rates but the effect is marginal. It is interesting to note that even at 20%, the kill rate is high. This can only be the case if the pellets are still palatable with this high concentration of active ingredient. Pellets of even higher concentration are difficult to manufacture without using additional binders.

In the following two Examples, the effect of varying the metal ion was investigated. In Example 7, the effect of varying the concentration of copper EDTA was investigated.

Summary

Examples 1 to 4 show that the Fe EDTA pellets worked well, the metaldehyde pellets worked moderately well, but the methiocarb and the Fe EDTA powder was less effective. However when using very moist potting mix fairly poor results for the powder would be expected as it would dissolve in the moisture and be taken up by the soil.

In Example 5, the efficacy of various concentrations of Fe EDTA were trialed.

Example 5

This Example was the same as Example 4, except that the treatments were control and pellets containing 1%, 2.5%, 6%, 9%, 12%, 16% and 20% Fe EDTA. The results are given in Table 5 below. The weather conditions were warm and dry and there was considerably less snail activity than in Example 2. Dead snails were removed and counted after 6 days. The lower kill rate (compared to Example 2) was expected as feeding was reduced.

TABLE 5

Comparison of the efficacies of varying concentrations of Fe EDTA used in the pellets.

| Control | 0/6 | 0/6 | 0/6 | 0/18 |
|---|---|---|---|---|
| Fe EDTA 1% | 2/6 | 0/6 | 1/6 | 3/18 |
| Fe EDTA 2.5% | 0/6 | 0/6 | 1/6 | 1/18 |
| Fe EDTA 6% | 2/6 | 2/6 | 4/6 | 8/18 |
| Fe EDTA 9% | 2/6 | 3/6 | 4/6 | 9/18 |
| Fe EDTA 12% | 3/6 | 3/6 | 5/6 | 11/18 |
| Fe EDTA 16% | 3/6 | 4/6 | 3/6 | 10/18 |
| Fe EDTA 20% | 6/6 | 3/6 | 4/6 | 13/18 |

Summary

The results of Example 5 indicate that the proposed 9% Fe EDTA is appropriate. Slightly higher concentrations may give slightly higher kill rates but the effect is marginal. It is interesting to note that even at 20%, the kill rate is high. This can only be the case if the pellets are still palatable with this high concentration of active ingredient. Pellets of even higher concentration are difficult to manufacture without using additional binders.

In the following two Examples, the effect of varying the metal ion was investigated. In Example 7, the effect of varying the concentration of copper EDTA was investigated.

In Example 8, the efficacy of a different metal chelate Fe EDDHA was compared to Fe EDTA.

Example 8

This Example was the same as Example 2, except that Fe EDDHA was also tested. The average daily maximum temperature was about 25° C. and the potting mix was kept moist by the addition of a 50 ml of water once a day. The dead snails were removed and counted after 8 days. The results are shown in Table 8 below.

TABLE 8

Comparison of the efficacies of 10% Fe EDDHA with 10% Fe EDTA

| Control | 1/6 | 0/6 | 0/6 | 0/6 | 1/24 |
|---|---|---|---|---|---|
| 10% Fe EDDHA | 3/6 | 2/6 | 0/6 | 3/6 | 8/24 |
| 10% Fe EDTA | 3/6 | 2/6 | 4/6 | 4/6 | 13/24 |

Summary

From this result, it can be seen that Fe EDTA is far more effective than Fe EDDHA.

Examples 9 to 11, the efficacy of different bait compositions and pellet size was compared.

Example 9

This Example used low bran formulation in two different sizes of pellet compared with a high bran formulation as against a control containing no active ingredient. Four different "plots" containing moist potting mix were used. The weather conditions for this trail were warm and dry. The dead snails were collected and counted after 7 days. The results are shown in Table 9.

TABLE 9

Comparison of efficacies of different bait compositions and pellet size.

| Control | 0/6 | 0/6 | 0/6 | 0/6 | 0/24 |
|---|---|---|---|---|---|
| Formulation 1 (low bran) 2 mm | 5/6 | 6/6 | 3/6 | 5/6 | 19/24 |
| Formulation 2 (low bran) 3.5 mm | 4/6 | 5/6 | 6/6 | 5/6 | 20/24 |
| Formulation 3 (low bran) 2 mm | 5/6 | 3/6 | 3/6 | 6/6 | 17/24 |
| Formulation 4 (high bran) 3.8 mm | 5/6 | 5/6 | 5/6 | 5/6 | 20/24 |

Example 10

This Example was the same as above except that moist sandy loam was used. The difference in medium appeared not to greatly alter the results obtained. However, a higher kill rate was observed when using a pellet size of around 3.5 mm, irrespective of the bait formulation used. The dead snails were collected and counted after 8 days. The results are shown in Table 10.

TABLE 10

Comparison of efficacy of different bait compositions and pellet size.

| Control | 0/6 | 0/6 | 0/6 | 0/6 | 0/24 |
|---|---|---|---|---|---|
| Formulation 1 (low bran) 2 mm | 5/6 | 5/6 | 3/6 | 5/6 | 18/24 |
| Formulation 2 (low bran) 3.5 mm | 4/6 | 5/6 | 6/6 | 5/6 | 20/24 |
| Formulation 3 (low bran) 2 mm | 5/6 | 3/6 | 3/6 | 6/6 | 17/24 |
| Formulation 4 (high bran) 3.8 mm | 5/6 | 5/6 | 5/6 | 5/6 | 20/24 |

Example 11

This Example utilised three "plots" which contained moist potting mix. The weather conditions were much cooler than the above two Examples. A low bran formulation contained in a small pellet and a high bran formulation contained in a larger pellet were compared to metaldehyde and methiocarb. The results are shown in Table 11.

TABLE 11

Comparison of the efficacies of metaldehyde, methiocarb and Fe EDTA pellets.

| Control | 0/6 | 0/6 | 0/6 | 0/18 |
|---|---|---|---|---|
| Bran formulation 1 (low bran) 2 mm | 4/6 | 4/6 | 3/6 | 11/18 |
| Bran formulation 4 (high bran) 3.8 mm | 4/6 | 5/6 | 6/6 | 15/18 |
| Metaldehyde | 2/6 | 0/6 | 1/6 | 3/18 |
| Methiocarb | 4/6 | 4/6 | 3/6 | 11/18 |

Summary

Examples 9 to 11 show that the low bran formulation of the invention worked as well as methiocarb, but the high bran formulation of the invention in the larger pellet was the most effective. Example 11 shows that metaldehyde does not work as well at the lower temperatures.

In Example 12, the efficacy of Fe EDTA with and without 10% paraffin wax used as a water-proofing agent, was compared to that of metaldehyde under different weather conditions, while Example 13 compared Fe EDTA pellets with and without 10% paraffin wax.

Example 12

For this Example, the bait formulation contained high bran and the weather conditions were cool. After 8 days, the dead snails in each plot were collected and counted. The results are shown in Table 12.

TABLE 12

Comparison of the efficacies of metaldehyde, Fe EDTA and Fe EDTA/10% paraffin wax pellets.

| Control | 0/5 | 0/5 | 0/5 | 0/15 |
|---|---|---|---|---|
| Metaldehyde | 0/5 | 0/5 | 1/5 | 1/15 |
| Fe EDTA | 4/5 | 4/5 | 4/5 | 12/15 |
| Fe EDTA/10% wax | 2/5 | 4/5 | 3/5 | 9/15 |

Example 13

This Example was carried out using moist sandy loam contained in four "plots," a high bran formulation and the same weather conditions as in Example 12. The dead snails were collected and counted after seven days. The results are shown in Table 13.

TABLE 13

Comparison of efficacy of Fe EDTA pellets with and without wax.

| Fe EDTA | 4/6 | 6/6 | 5/5 | 5/6 | 20/23 |
|---|---|---|---|---|---|
| Fe EDTA/10% wax | 5/6 | 5/6 | 5/6 | 3/6 | 18/24 |

Summary

The results showed that a lower kill rate was obtained for the pellets containing paraffin wax than those without paraffin wax, but the pellets containing Fe EDTA and 10% paraffin wax were much more effective than metaldehyde.

In Examples 14 and 15, a $C_{16}$–$C_{18}$ alcohol known as HYDRENOL MY, 5% by weight, was incorporated into the high bran bait formulation as a water-proofing agent. In both Examples, trials were carried out in cold weather conditions. The efficacy of Fe EDTA without the water-proofing agent and Fe EDTA including the water-proofing agent were compared with metaldehyde (1.5%) and methiocarb (2%), respectively in Example 14 and then with each other in Example 15.

Example 14

In this Example, seven "plots" for each molluscicide formulation and for the control were used. The variety of snail was Helix aspersa. The dead snails were collected and counted after 10 days. The results are shown in Table 14.

TABLE 14

Comparison of the efficacy of Fe EDTA with and without waterproofing for *Helix aspersa*.

| Control | 0/6 | 0/6 | 0/6 | 0/6 | 0/6 | 0/6 | 0/6 | 0/42 |
|---|---|---|---|---|---|---|---|---|
| Fe EDTA | 2/6 | 2/6 | 2/6 | 1/6 | 2/6 | 1/6 | 2/6 | 12/42 |
| Fe EDTA + 5% HYD MY | 3/6 | 1/6 | 2/6 | 2/6 | 2/6 | 1/6 | 2/6 | 13/42 |

Example 15

In this Example, eight "plots" for each molluscicide formulation were used. The variety of slug used was *Deroceras reticulatum*. The dead slugs were collected and counted after 10 days. The number of slugs that could not be found are given in brackets. The results are shown in Table 15.

TABLE 15

Comparison of the efficacies of Fe EDTA, Fe EDTA with waterproofing, metaldehyde and metbiocarb pellets for *Deroceras reticulatum*.

| Control | 0/2 | 0/2 | 0/2 | 0/2 | 0/2 | 1/2 | 0/2 | 0/2 | 1/16 |
|---|---|---|---|---|---|---|---|---|---|
| Metaldehyde | 2/2 | 1/2 | 0/2 | 0/2 | 1/2 | 0/2 | 0/2 | 0(1)/2 | 7(1)/16 |
| Methiocarb | 2/2 | 2/2 | 1/2 | 2/2 | 1(1)/2 | 1(1)/2 | 2/2 | 1/2 | 15(1)/16 |
| Fe EDTA | 2/2 | 2/2 | 1(1)/2 | 0(1)/2 | 2/2 | 2/2 | 2/2 | 2/2 | 15(2)/18 |
| Fe EDTA/ 5% HYD MY | 2/2 | 2/2 | 2/2 | 2/2 | 1(1)/2 | 2/2 | 2/2 | 2/2 | 15(1)/16 |

Summary

Examples 14 and 15 show that the bait formulation including the water-proofing agent actually worked better than those without. Also, the water-proofed complexone worked as well as methiocarb which both worked better than metaldehyde. Thus, the inclusion of the water-proofing agent does not dramatically affect the efficacy of the present invention.

In Example 16, the efficacies of various concentrations of Fe EDTA were trialed on the slug species, *Deroceras reticulatum*.

Example 16

In this Example, six "plots" were used under cool weather conditions, using a high bran bait formulation, with carrot as the feed. The soil type was sandy loam and the slug species was *Deroceras reticulatum*. The number of dead slugs were collected and counted after seven days. The results are given in Table 16.

TABLE 16

Comparison of the efficacies of various concentrations of Fe EDTA for *Deroceras reticulatum*

| Control | 0/2 | 0/2 | 1/2 | 0/2 | 0/2 | 0/2 | 1/12 |
|---|---|---|---|---|---|---|---|
| Fe EDTA 4.8% | 1/2 | 0/2 | 1/2 | 2/2 | 1/2 | 2/2 | 7/12 |
| Fe EDTA 5.7% | 2/2 | 1/2 | 1/2 | 2/2 | 2/2 | 2/2 | 10/12 |
| Fe EDTA 9% | 2/2 | 1/2 | 2/2 | 2/2 | 2/2 | 2/2 | 11/12 |

Summary

Fe EDTA at a concentration of 9% was found to be the most effective.

In Examples 17 to 26, trials involving different species of snails and slugs were carried out to test the efficacy of Fe EDTA pellets compared with the control. Moist potting mix was used in all Examples.

Example 17

In this Example, three "plots" were used under warm weather conditions. The feed was 20% bran and 80% wheat flour and the bait formulation included low bran. The species of snail was *Cernuella virgata*. The dead snails were collected and counted after 8 days. The results are shown in Table 17.

TABLE 17

The efficacy of Fe EDTA pellets for *Cernuella virgata*.

| Control | 0/5 | 0/5 | 0/5 | 0/15 |
|---|---|---|---|---|
| Fe EDTA | 2/5 | 4/5 | 3/5 | 9/15 |

Example 18

In this Example, four "plots" were set up under cooler conditions than in Example 17. The feed was lettuce and the bait formulation included high bran. The species of snail was Cochlicella spp. The dead snails were collected and counted after 7 days. The results are shown in Table 18.

TABLE 18

The efficacy of Fe EDTA pellets for *Cochlicella* spp.

| Control | 1/10 | 1/10 | 1/10 | 2/10 | 5/40 |
|---|---|---|---|---|---|
| Fe EDTA | 10/10 | 10/10 | 9/10 | 10/10 | 39/40 |

Example 19

In this Example, ten "plots" were set up under similar conditions to Example 18. The feed was bran and the bait formulation included high bran. The species of snail was *Theba pisana*. The efficacy of Fe EDTA (9%), Fe EDTA (9%) +HYDRENOL MY (5%), metaldehyde (DEFENDER™ brand) and methiocarb (BAYSOL® brand) were compared to a control. The dead snails were collected and counted after 13 days. The results are shown in Table 19.

TABLE 19

Comparison of the efficacies of Fe EDTA (9%) and Fe EDTA (9%) + waterproof (5%) pellets with methiocarb (BAYSOL ®) and metaldehyde (DEFENDER ™) for *Theba pisana*.

| Control | 0/5 | 1/5 | 0/5 | 0/5 | 0/5 | 0/5 | 1/5 | 2/5 | 0/5 | 0/5 | 4/50 |
|---|---|---|---|---|---|---|---|---|---|---|---|
| Methiocarb (BAYSOL ®) | 4/5 | 3/5 | 4/5 | 5/5 | 4/5 | 5/5 | 5/5 | 5/5 | 3/5 | 3/5 | 38/50 |
| Metaldehyde (DEFENDER ™) | 4/5 | 3/5 | 2/5 | 4/5 | 4/5 | 3/5 | 4/5 | 2/5 | 5/5 | 5/5 | 36/50 |
| Fe EDTA (9%) | 4/5 | 5/5 | 5/5 | 5/5 | 4/5 | 5/5 | 5/5 | 5/5 | 3/5 | 4/5 | 45/50 |
| Fe EDTA (9%) + 5% HYD MY | 2/5 | 2/5 | 4/5 | 2/5 | 3/5 | 4/5 | 4/5 | 3/5 | 4/5 | 3/5 | 31/50 |

Example 20

In this Example, eight "plots" were used in cool weather conditions. The bait formulation included high bran, while the feed was carrot. As above, the species of snail was *Theba pisana* and the soil was sandy loam. The dead snails were removed and counted after 7 days. The results are shown in Table 20.

TABLE 20

Comparison of the efficacies of Fe EDTA (2%, 3%, 3.8%, 4.8%, 5.7%, 7.4%, 9%), Q-Fe-6, Fe-Hi, Fe DPTA pellets with methiocarb (BAYSOL ®), metaldehyde (DEFENDER ™), metaldehyde (DEFENDER ™ Petrepel), metaldehyde (Lonza) for *Theba pisana*.

| Control | 0/5 | 1/5 | 0/5 | 0/5 | 1/5 | 1/5 | 0/5 | 3/35 |
|---|---|---|---|---|---|---|---|---|
| Fe EDTA 2% | 2/5 | 1/5 | 1/5 | 2/5 | 4/5 | 1/5 | 1/5 | 12/35 |
| Fe EDTA 3% | 0/5 | 0/5 | 3/5 | 2/5 | 2/5 | 1/5 | 3/5 | 11/35 |
| Fe EDTA 3.8% | 4/5 | 2/5 | 1/5 | 2/5 | 0/5 | 1/5 | 1/5 | 11/35 |
| Fe EDTA 4.8% | 2/5 | 0/5 | 3/5 | 0/5 | 3/5 | 1/5 | 1/5 | 10/35 |
| Fe EDTA 5.7% | 4/5 | 4/5 | 3/5 | 4/5 | 3/5 | 3/5 | 3/5 | 24/35 |
| Fe EDTA 7.4% | 3/5 | 3/5 | 2/5 | 4/5 | 2/5 | 4/5 | 1/5 | 17/35 |
| Fe EDTA 9% | 1/5 | 3/5 | 5/5 | 4/5 | 4/5 | 3/5 | 2/5 | 22/35 |
| Q-Fe-6 | 0/5 | 1/5 | 0/5 | 0/5 | 0/5 | 0/5 | 0/5 | 1/35 |
| Fe-Hi | 1/5 | 0/5 | 0/5 | 0/5 | 0/5 | 0/5 | 0/5 | 1/35 |
| Fe DPTA | 2/5 | 2/5 | 1/5 | 1/5 | 0/5 | 2/5 | 2/5 | 10/35 |
| Methiocarb BAYSOL ® | 1/5 | 1/5 | 3/5 | 3/5 | 2/5 | 3/5 | 0/5 | 13/35 |
| Metaldehyde DEFENDER ™ | 2/5 | 2/5 | 1/5 | 1/5 | 0/5 | 1/5 | 1/5 | 8/35 |
| Metaldehyde DEFENDER ™ Petrepel | 0/5 | 0/5 | 2/5 | 0/5 | 0/5 | 1/5 | 1/5 | 4/35 |
| Metaldehyde Lonza | 2/5 | 2/5 | 0/5 | 1/5 | 0/5 | 0/5 | 0/5 | 5/35 |

Q-Fe-6 is ferric sodium ethylenediamine bis[(2-hydroxyphenyl)acetic acid] (Akzo Chemicals)
Fe-Hi is ferric sodium ethylenediamine bis[(2-hydroxyphenyl)acetic acid] (Allied Colloids)
Fe DPTA is ferric sodium diethylenetriamine pentaacetic acid.

Example 21

In this Example, seven "plots" were used in cool weather conditions. The bait formulation included high bran, while the feed was carrot. The soil type was moist potting mix. The species of snail was *Helix aspersa*. The number of snails dead after eight days were removed and counted. The efficacy of Fe EDTA was compared to that of DEFENDER™ Petrepel. The results are given in Table 21.

TABLE 21

Comparison of the efficacy of Fe EDTA with DEFENDER ™ Petrepel on *Helix aspersa*.

| Control | 0/6 | 0/6 | 0/6 | 0/6 | 0/6 | 0/6 | 0/6 | 0/42 |
|---|---|---|---|---|---|---|---|---|
| DEFENDER ™ Petrepel | 0/6 | 0/6 | 1/6 | 0/6 | 1/6 | 0/6 | 0/6 | 2/42 |
| Fe EDTA | 4/6 | 2/6 | 5/6 | 0/6 | 3/6 | 5/6 | 1/6 | 20/42 |

Example 22

In this Example, six "plots" were used in cool weather conditions. The bait formulation included high bran. The species of snail was *Cochlicella barbara*. The efficacy of Fe EDTA was compared with that of methiocarb and metaldehyde. The results are shown in Table 22.

TABLE 22

Comparison of the efficacies of Fe EDTA, methiocarb and metaldehyde pellets for *Cochlicella barbara*.

| Control | 2/10 | 1/10 | 2/10 | 2/10 | 3/10 | 3/10 | 12/60 |
|---|---|---|---|---|---|---|---|
| Methiocarb | 6/9 | 8/10 | 6/10 | 6/10 | 8/10 | 5/10 | 39/59 |
| Metaldehyde | 7/10 | 2/10 | 3/10 | 7/10 | 3/9 | 4/10 | 26/59 |
| Fe EDTA | 8/10 | 5/9 | 5/9 | 7/10 | 6/10 | 7/10 | 38/58 |

Example 23

In this Example, six "plots" were used under warm weather conditions. The bait formulation included low bran. The species of slug was *Deroceras reticulatum*. The dead slugs were collected and counted after 8 days. The results are shown in Table 23.

TABLE 23

The efficacy of Fe EDTA pellets for *Deroceras reticulatum*.

| Control. | 1/6 | 1/6 | 1/6 | 1/6 | 1/6 | 1/6 | 5/36 |
|---|---|---|---|---|---|---|---|
| Fe EDTA | 6/6 | 6/6 | 6/6 | 6/6 | 6/6 | 6/6 | 36/36 |

Example 24

In this Example, six "plots" were used in moderate to warm weather conditions: The bait formulation included high bran. The species of slug was *Limax maximus*. The dead slugs were collected and counted after 7 days. The results are shown in Table 24.

TABLE 24

The efficacy of Fe EDTA pellets for *Limax maximus*.

| Control | 0/6 | 0/6 | 0/6 | 0/6 | 0/6 | 0/6 | 0/36 |
|---|---|---|---|---|---|---|---|
| Fe EDTA | 6/6 | 6/6 | 6/6 | 6/6 | 6/6 | 6/6 | 36/36 |

Example 25

In this Example, juvenile slugs of Deroceras reticulatun, being 1 to 2 cm long were subjected to Fe EDTA. The number of dead slugs were collected and counted after 9 days. The number in brackets denotes the number of slugs that were not found. The results are shown in Table 25.

TABLE 25

The efficacy of Fe EDTA pellets for juvenile slugs.

| Control | 0(2)/2 | 0/2 | 0/2 | 0/2 | 0(2)/2 | 0/2 | 0(4)/12 |
|---|---|---|---|---|---|---|---|
| Fe EDTA | 2/2 | 1(1)/2 | 2/2 | 2/2 | 1(1)/2 | 1/2 | 9(2)/12 |

Summary

The results show that Fe EDTA is effective even for all molluscs trialed including juvenile slugs.

In Examples 26 and 27, the efficacy of Fe EDTA (9% in a high bran formulation) is compared to other well-known brands of snail and slug killers containing methiocarb or metaldehyde. In both Examples, cool weather conditions were employed.

Example 26

In this Example, the efficacy of Fe EDTA was compared with that of Blitzem made by Yates (1.5% metaldehyde), Lonza (6% metaldehyde) and BAYSOL® made by Bayer (2% methiocarb). The dead snails were collected and counted after 8 days. The results are shown in Table 26.

TABLE 26

Comparison of the efficacy of Fe EDTA with that of metaldehyde (1.5%), metaldehyde (5%) and metaldehyde (6%).

| Control | 0/6 | 0/6 | 0/6 | 0/6 | 0/6 | 0/6 | 0/6 | 0/6 | 0/6 | 0/6 | 0/60 |
|---|---|---|---|---|---|---|---|---|---|---|---|
| Metaldehyde (1.5%) Blitzem | 1/6 | 0/6 | 0/6 | 0/6 | 0/6 | 0/6 | 0/6 | 0/6 | 0/6 | 0/6 | 1/60 |
| Metaldehyde (6%) Lonza | 0/6 | 1/6 | 1/6 | 1/6 | 1/6 | 0/6 | 0/6 | 0/6 | 1/6 | 0/6 | 5/60 |
| Methiocarb (2%) BAYSOL® | 3/6 | 2/6 | 1/6 | 4/6 | 4/6 | 2/6 | 3/6 | 2/6 | 3/6 | 2/6 | 26/60 |
| Fe EDTA | 4/6 | 4/6 | 5/6 | 4/6 | 1/6 | 1/6 | 4/6 | 3/6 | 4/6 | 4/6 | 38/60 |

Example 27

In this Example, the efficacy of Fe EDTA was compared with that of BIO® Slug-Gard (4% methiocarb, a UK product) and GARDENER'S CHOICE™ (metaldehyde, a brand available in K-Mart stores) for *Helix asperse*. The dead snails were collected and counted after 10 days. The results are shown in Table 27.

TABLE 27

Comparison of the efficacies of Fe EDTA, metaldehyde and methiocarb pellets for *Helix aspersa*.

| Control | 0/6 | 0/6 | 1/6 | 0/6 | 0/6 | 0/6 | 0/6 | 0/6 | 1/48 |
|---|---|---|---|---|---|---|---|---|---|
| Metaldehyde GARDENER'S CHOICE ™ | 1/6 | 0/6 | 0/6 | 0/6 | 0/6 | 0/6 | 1/6 | 0/6 | 2/48 |
| Methiocarb BIO® Slug-Gard | 1/6 | 1/6 | 2/6 | 1/6 | 0/6 | 2/6 | 1/6 | 2/6 | 10/48 |
| Fe EDTA | 2/6 | 4/6 | 2/6 | 2/6 | 4/6 | 2/6 | 2/6 | 0/6 | 18/48 |

Summary

Examples 26 and 27 both show that a 9% Fe EDTA formulation is a far more effective molluscicide than any other brand used in the experiments.

In Examples 28 and 29, a comparison of various chelate compositions was carried out.

Example 28

In this Example, the efficacies of Fe EDTA, ferric sodium diethylenetriaminepentaacetic acid (here referred to as D—Fe-11) and ferrous sulphate+EDTA were compared to a control. The weather conditions were cool and a high bran formulation was used. The dead snails were collected and counted after 8 days. The results are shown in Table 28.

TABLE 28

Comparison of the efficacies of Fe EDTA, D-Fe-11 and $FeSO_4$ + $Na_2EDTA$.

| Control | 0/6 | 0/6 | 0/6 | 0/6 | 0/6 | 0/6 | 0/36 |
|---|---|---|---|---|---|---|---|
| D-Fe-11 | 0/6 | 1/6 | 1/6 | 0/6 | 0/6 | 0/6 | 2/36 |
| $FeSO_4$* + $Na_2EDTA$ | 0/6 | 0/6 | 0/6 | 0/6 | 0/6 | 0/6 | 0/36 |
| Fe EDTA | 3/6 | 3/6 | 1/6 | 0/6 | 0/6 | 1/6 | 8/36 |

*same Fe conc as in Fe EDTA ratio of $FeSO_4$:$Na_2EDTA$ to give ferrous disodium EDTA. D-Fe-11 is ferric sodium diethylenetriaminepentaacetic acid.

Example 29

In this Example, the efficacies of Fe EDTA, ferric sodium ethylenediamine bis[(2-hydroxyphenyl)acetic acid] (here referred to as Q—Fe-6) (Akzo Chemicals) and ferrous sulphate+$Na_2EDTA$ were compared. The same conditions as in Example 28 were employed. The results are shown in Table 29.

TABLE 29

Comparison of the efficacies of Fe EDTA, Q-Fe-6 and $FeSO_4$ + $Na_2EDTA$.

| Control | 0/6 | 0/6 | 0/6 | 0/6 | 0/6 | 0/30 |
|---|---|---|---|---|---|---|
| Q-Fe-6 | 1/6 | 2/6 | 0/6 | 0/6 | 1/6 | 4/30 |
| $FeSO_4$ + $Na_2EDTA$ | 0/6 | 0/6 | 0/6 | 0/6 | 0/6 | 0/30 |
| Fe EDTA | 2/6 | 3/6 | 4/6 | 3/6 | 2/6 | 14/30 |

Summary

The results from Examples 28 and 29 suggest that the composition of $FeSO_4$+$Na_2EDTA$ was totally ineffective as a molluscicide. An investigation carried out on this composition revealed that it had a very low pH and the likely explanation for its ineffectiveness is that it is unattractive to molluscs. These Examples also illustrate that altering the chelating ligand results in a more effective molluscicide than the $FeSO_4$+$Na_2EDTA$ composition, but a less effective molluscicide than Fe EDTA.

The results of the above two Examples led to the investigation illustrated in Examples 30 to 32 of the dependence of the efficacy on pH. These investigations utilised various aluminium and Fe(II) chelate formulations, compared with the Fe(III) EDTA formulation. Various concentrations of $K_2CO_3$ were added to adjust the pH of the compositions trialed The various formulations used were as follows:

Formulations A to E were made up from $FeSO_4$+$Na_2EDTA$+$K_2CO_3$

Formulation A 0.65% Fe as Fe(II)ETDA+4.8% $K_2CO_3$ pH=9.5

Formulation B 0.65% Fe as Fe(II)EDTA+2.0% $K_2CO_3$ pH=7.8

Formulation C 0.55% Fe as Fe(II)EDTA+1.0% $K_2CO_3$ pH=6.8

Formulation D 0.70% Fe as Fe(II)EDTA+2.0% $K_2CO_3$ pH=6.5

Formulation E 1.80% Fe as Fe(II)EDTA+4.5% $K_2CO_3$ pH=7

Formulations F to J were all aluminium chelate formulations.

Formulation F 1.1% Al as aluminium potassium salt of EDTA

Formulation G 0.55% Al as aluminium potassium salt of trans-1,2-diaminocyclohexane-N,N,N',N'-tetraacetic acid Formulation I 1.1% Al as aluminium potassium salt of 1,3-diamino-2-hydroxypropane-N,N,N',N'-tetraacetic acid Formulation J 1.2% Al as aluminium potassium salt of 1,2-diaminopropane-N,N,N',N'-tetraacetic acid Example 30

In this Example, the variety of snail used was *Helix aspersa* within a temperature range of 18–29° C., using a high bran formulation. The dead snails were removed and counted after 7 days. The results are shown in Table 30.

TABLE 30

Comparison of the efficacies of various aluminium and iron chelate formulations.

| Control | 0/3 | 0/3 | 0/3 | 0/3 | 0/3 | 0/3 | 0/3 | 0/3 | 0/24 |
|---|---|---|---|---|---|---|---|---|---|
| Formulation A | 3/3 | 3/3 | 3/3 | 3/3 | 2/3 | 3/3 | 2/3 | 3/3 | 22/24 |
| Formulation B | 0/3 | 3/3 | 1/3 | 0/3 | 1/3 | 2/3 | 3/3 | 3/3 | 13/24 |
| Formulation C | 1/3 | 2/3 | 3/3 | 1/3 | 1/3 | 3/3 | 2/3 | 3/3 | 16/24 |
| Formulation D | 1/3 | 3/3 | 3/3 | 3/3 | 3/3 | 3/3 | 3/3 | 1/3 | 20/24 |

TABLE 30-continued

Comparison of the efficacies of various aluminium and iron chelate formulations.

| | | | | | | | | | |
|---|---|---|---|---|---|---|---|---|---|
| Formulation E | 2/3 | 0/3 | 1/3 | 1/3 | 1/3 | 0/3 | 0/3 | 1/3 | 6/24 |
| Formulation F | 0/3 | 0/3 | 1/3 | 0/3 | 1/3 | 3/3 | 0/3 | 1/3 | 6/24 |

Example 31

In this Example, the variety of snail employed was *Theba pisana*. The trial was conducted within a temperature range of 18–23° C., using a high bran bait formulation. The dead snails were removed and counted after 7 days. The results are shown in Table 31.

TABLE 31

Comparison of the efficacies of various aluminium and Fe EDTA formulations.

| | | | | | | | | | |
|---|---|---|---|---|---|---|---|---|---|
| Control | 0/6 | 0/6 | 2/6 | 0/6 | 0/6 | 0/6 | 0/6 | 0/6 | 2/48 |
| Formulation E | 6/6 | 6/6 | 5/6 | 4/6 | 5/6 | 5/6 | 4/6 | 4/6 | 39/48 |
| Formulation F | 2/6 | 1/6 | 2/6 | 2/6 | 2/6 | 0/6 | 2/6 | 2/6 | 13/48 |
| Formulation I | 2/6 | 0/6 | 0/6 | 0/6 | 0/6 | 0/6 | 0/6 | 0/6 | 2/48 |
| Formulation J | 1/6 | 1/6 | 0/6 | 1/6 | 0/6 | 2/6 | 2/6 | 0/6 | 7/48 |

Example 32

In this Example, the conditions employed were the same as for Example 31, except that the variety of snail employed was *Helix aspersa*. The dead snails were removed and collected after 7 days. The results are shown in Table 32.

TABLE 32

Comparison of the efficacies of various aluminium and iron chelate formulations.

| | | | | | | | | | |
|---|---|---|---|---|---|---|---|---|---|
| Control | 0/6 | 0/6 | 0/6 | 0/6 | 0/6 | 0/6 | 0/6 | 0/6 | 0/48 |
| Formulation E | 3/6 | 3/6 | 2/6 | 5/6 | 2/6 | 1/6 | 2/6 | 4/6 | 22/48 |
| Formulation F | 1/6 | 0/6 | 0/6 | 1/6 | 0/6 | 0/6 | 0/6 | 0/6 | 2/48 |
| Formulation G | 0/6 | 2/6 | 0/6 | 0/6 | 1/6 | 1/6 | 0/6 | 0/6 | 4/48 |
| Formulation H | 1/6 | 0/6 | 0/6 | 0/6 | 0/6 | 0/6 | 0/6 | 0/6 | 1/48 |
| Formulation I | 0/6 | 0/6 | 0/6 | 0/6 | 0/6 | 0/6 | 0/6 | 0/6 | 0/48 |
| Formulation J | 1/6 | 0/6 | 0/6 | 1/6 | 0/6 | 2/6 | 1/6 | 0/6 | 5/48 |
| 9% Fe EDTA | 5/6 | 6/6 | 5/6 | 6/6 | 6/6 | 6/6 | 5/6 | 5/6 | 44/48 |

Summary

The results from Examples 30 to 32 show that 9% ferric EDTA is the most effective composition of those chosen for trial. The aluminium chelates were found to be not particularly effective, although of those trialed, the EDTA complex appears to have been the most successful.

Example 33

In this Example, the efficacies of various concentrations of ferrous EDTA were compared with 9% ferric EDTA (pH of about 7), Zeneca (a U.K. product containing 4% metaldehyde), PBI (a U.K. product containing approximately 3% metaldehyde) and Pets' Choice 50% (based on a mustard seed by-product recently introduced onto the Australian market). The snail variety was *Helix aspersa* and the temperature range at which the trial was conducted was 18–26° C. The results are shown in Table 33;

The various concentrations of Fe(II) EDTA had the following pH values and were adjusted with $K_2CO_3$:

8.9% Fe(II) EDTA pH=5.6
8.7% Fe(II) EDTA pH=5.7
8.6% Fe(II) EDTA pH=6.2

TABLE 33

Comparison of the efficacies of various concentrations of Fe(II) EDTA, 9% Fe(III) EDTA, Zeneca, PBI and Pets' Choice.

| | | | | | | | | |
|---|---|---|---|---|---|---|---|---|
| Control | 0/6 | 0/6 | 0/6 | 0/6 | 1/6 | 0/6 | 0/6 | 1/36 |
| 9% Fe(III) EDTA | 3/6 | 3/6 | 4/6 | 3/6 | 4/6 | 2/6 | 4/6 | 20/36 |
| Zeneca | 3/6 | 2/6 | 2/6 | 2/6 | 1/6 | 0/6 | 0/6 | 10/36 |
| PBI | 0/6 | 2/6 | 0/6 | 1/6 | 1/6 | 0/6 | 1/6 | 5/36 |
| Pets' Choice 50% | 3/6 | 4/6 | 3/6 | 2/6 | 4/6 | 1/6 | 1/6 | 18/36 |
| 8.9% Fe(II) EDTA | 5/6 | 4/6 | 1/6 | 1/6 | 1/6 | 1/6 | 1/6 | 14/36 |
| 8.7% Fe(II) EDTA | 6/6 | 2/6 | 3/6 | 6/6 | 4/6 | 0/6 | 0/6 | 21/36 |
| 8.6% Fe(II) EDTA | 4/6 | 5/6 | 1/6 | 3/6 | 2/6 | 2/6 | 2/6 | 19/36 |

Summary

It can be seen from this study that 8.6% and 8.7% Fe(II) EDTA are just as effective as 9% Fe(III) EDTA and all the formulations containing chelates are more effective as a molluscicide than Zeneca or PBI.

Example 34

In this Example, the efficacies of baits containing various concentrations of $K_2CO_3$ and Fe(III) EDTA were compared with that of 9% Fe(III) EDTA. The temperature range at which the trial was conducted was 17–26° C. and the snail variety was *Helix aspersa*. The results are shown in Table 34.

The pH's of the various formulations were as follows:

Formulation 1 40 g bran/flour+0.00376 mole $K_2CO_3$+3.5 g Fe EDTA pH=7.3 (8% Fe(OH)EDTA)

Formulation 2 40 g bran/flour+0.00752 mole $K_2CO_3$+3.5 g Fe EDTA pH=7.8 (8% Fe(OH)EDTA)

Formulation 3 40 g bran/flour+0.01113 mole $K_2CO_3$+3.32 g Fe EDTA pH=10.0 (7.7% Fe(OH)EDTA)

Formulation 4 40 g bran/flour+0.0151 mole $K_2CO_3$+3.25 g Fe EDTA pH=10.33 (7.6% Fe(OH)EDTA)

TABLE 34

Comparison of the efficacies of baits containing various concentrations of $K_2CO_3$ and Fe(III) EDTA with 9% Fe(III) EDTA.

| | | | | | | | | |
|---|---|---|---|---|---|---|---|---|
| Control | 0/6 | 1/6 | 0/6 | 0/6 | 0/6 | 0/6 | 0/6 | 1/48 |
| 9% Fe EDTA | 5/6 | 6/6 | 4/6 | 4/6 | 6/6 | 3/6 | 4/6 | 5/6 | 37/48 |
| Formulation 1 | 6/6 | 5/6 | 4/6 | 4/6 | 4/6 | 2/6 | 3/6 | 4/6 | 28/48 |
| Formulation 2 | 2/6 | 3/6 | 1/6 | 2/6 | 3/6 | 3/6 | 6/6 | 4/6 | 24/48 |
| Formulation 3 | 6/6 | 3/6 | 2/6 | 2/6 | 0/6 | 3/6 | 2/6 | 2/6 | 20/48 |
| Formulation 4 | 2/6 | 3/6 | 2/6 | 2/6 | 2/6 | 2/6 | 5/6 | 4/6 | 22/48 |

Example 35

In this Example, the efficacies of baits having various concentrations of Al EDTA and different pH's were compared with baits having various concentrations of Fe EDTA. The temperature range at which the trial was conducted was 17–20° C. and the snail variety was *Helix aspersa*. The results are shown in Table 35.

The pH's of the various formulations were as follows:

Formulation 5 20 g bran/flour+0.1801 g Al EDTA pH=9.37 (0.78% Al)

Formulation 6 20 g bran/flour+0.2390 g Al EDTA pH=6.80 (1.04% Al)

Formulation 7 20 g bran/flour+0.2662 g Al EDTA pH=8.63 (1.11% Al)

Formulation 8 20 g bran/flour+0.1405 g Al EDTA pH=6.85 (0.62% Al)

TABLE 35

Comparison of the efficacies of baits containing various concentrations of Fe(III) EDTA and Al EDTA.

| | | | | | | | | | |
|---|---|---|---|---|---|---|---|---|---|
| Control | 0/3 | 0/3 | 1/3 | 1/3 | 1/3 | 0/3 | 2/3 | 0/3 | 5/24 |
| Formulation 1 | 2/3 | 1/1 | 1/1 | 2/3 | 1/1 | 1/1 | 1/1 | 2/3 | 11/14 |
| Formulation 2 | 3/3 | 2/3 | 2/3 | 1/3 | 2/3 | 2/3 | 2/3 | 1/3 | 15/24 |
| Formulation 3 | 2/3 | 2/3 | 2/3 | 3/3 | 2/3 | 2/3 | 2/3 | 2/3 | 17/24 |
| Formulation 4 | | | | | | | | | |
| Formulation 5 | 3/3 | 3/3 | 3/3 | 2/3 | 1/2 | 2/3 | 2/3 | 3/3 | 19/23 |
| Formulation 6 | 3/3 | 2/3 | 2/3 | 2/3 | 2/3 | 2/2 | 1/2 | 2/3 | 16/22 |
| Formulation 7 | 1/3 | 2/3 | 2/3 | 2/3 | 2/3 | 3/3 | 2/3 | 2/3 | 16/24 |
| Formulation 8 | 3/3 | 3/3 | 3/3 | 3/3 | 2/3 | 1/2 | 2/3 | 3/3 | 20/23 |

Summary

It appears from the results in Examples 34 and 35 that both the Fe(III)OH EDTA and Al EDTA formulations are effective for *Helix aspersa*. Previously, when the pH of the Al EDTA had not been adjusted, resulting in a very acidic composition (pH less than 4), it did not appear to work. The efficacy is not very pH dependent for near neutral and midly alkaline, but it is poor at low pH. The composition using Al(OH), and $Na_2EDTAH_2$ with no $CaCO_3$ or $K_2CO_3$ added as a filler has a very low pH and its efficacy is correspondingly low. As the amount of $K_2CO_3$ is increased, the pH is increased with a corresponding increase in efficacy. It appears that mixtures of $FeSO_4+NaEDTA+K_2CO_3$, (particularly the composition of Formulation A i.e. 0.65% Fe as Fe(II)EDTA+4.8% $K_2CO_3$) offer an alternative stomach poison, the efficacy of which appears to be similar to that of ferric EDTA and certainly superior to the incorporation of aluminium chelates.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The claims defining the invention are as follows:

1. A method of preparation of a stomach-action molluscicide comprising a an iron (II)- or Iron (III)-containing metal complexone and a carrier therefor, comprising the steps of:
   (i) blending the components together to form a blended composition;
   (ii) heating the blended composition for about 1 to 5 minutes in the presence of steam at an ambient temperature of between about 80 and 100° C.;
   (iii) maintaining the composition at the ambient temperature between about 10 and 30 seconds; and
   (iv) forming the blended composition into one or more pellets.

2. The method of preparation of a molluscicide according to claim 1, wherein step (ii) is carried out at a temperature of about 90° C. for about 2 minutes.

3. The method according to claim 2, wherein step (iii) is carried out for about 15 seconds.

4. The method according to claim 3, wherein step (iv) is carried out under pressure.

5. The stomach-action molluscicide pellet produced according to the method of claim 1.

6. The stomach-action molluscicide pellet produced according to the method of claim 1, wherein the pellet size is between about 2.5 and about 4 mm.

7. The stomach-action molluscicide pellet according to claim 6, wherein the pellet size is about 3 mm.

8. The method of preparation of a molluscicide according to claim 1, wherein said iron (II)- or iron (III)-containing metal complexone is $[FeEDTA]^-$, $[Fe(OH)EDTA]^{2-}$, ferric EDDHA, or ferric DTPA.

* * * * *